United States Patent [19]

Krutak et al.

[11] Patent Number: 5,235,047
[45] Date of Patent: Aug. 10, 1993

[54] BATHOCHROMIC AZO DYES DERIVED FROM 2-AMINOTHIOPHENES AND 2-AMINOTHIAZOLES

[75] Inventors: James J. Krutak; Max A. Weaver, both of Kingsport, Tenn.

[73] Assignee: Eastman Kodak Company, Rochester, N.Y.

[21] Appl. No.: 940,132

[22] Filed: Sep. 3, 1992

Related U.S. Application Data

[62] Division of Ser. No. 746,821, Aug. 19, 1991, Pat. No. 5,179,207.

[51] Int. Cl.$^5$ ............... C09B 29/039; C09B 29/033; C09B 29/36; D06P 1/18
[52] U.S. Cl. .................. 534/768; 534/775; 534/565; 534/807
[58] Field of Search ............... 534/768, 775

[56] References Cited

U.S. PATENT DOCUMENTS

| | | | |
|---|---|---|---|
| 3,055,910 | 9/1962 | Dickson et al. | 260/306.8 |
| 4,118,390 | 10/1978 | Wu et al. | 260/306.8 |
| 4,500,343 | 2/1985 | Burow, Jr. | 71/76 |
| 4,524,123 | 6/1985 | Schenk et al. | 430/241 |
| 4,643,758 | 2/1987 | Burow, Jr. et al. | 71/90 |
| 4,720,493 | 1/1988 | Kawakita | 514/230 |
| 4,841,036 | 6/1989 | Imahori et al. | 534/761 |

FOREIGN PATENT DOCUMENTS

| | | | |
|---|---|---|---|
| 335234 | 3/1988 | European Pat. Off. | 534/775 |
| 57-175189 | 4/1981 | Japan | 534/768 |
| 2185491 | 7/1987 | United Kingdom | 534/768 |

OTHER PUBLICATIONS

Weaver and Shuttleworth, Dyes and Pigments, pp. 81–121, (1982).
Martin, et al., J. Org. Chem., 26, 2032 (1961).
Wiley, et al., J. Am. Chem. Soc. 90, 1385–8, (1958).

*Primary Examiner*—Floyd D. Higel
*Attorney, Agent, or Firm*—Bernard J. Graves, Jr.; William P. Heath, Jr.

[57] ABSTRACT

Provided are certain bathochromic azo dyes which are prepared by reacting 2-aminothiphenes or 2-aminothiazoles, which contain a primary amino group, with 2-chloro-3-negatively-substituted maleimides. These compounds are then diazotized and coupled with azo components, for example, anilines, 1,2,3,4-tetrahydroquinolines, 2,3-dihydroindiles, and 3,4-dihydro-2H-1,4-benzoxazines to form blue-cyan azo dyes.

6 Claims, No Drawings

BATHOCHROMIC AZO DYES DERIVED FROM 2-AMINOTHIOPHENES AND 2-AMINOTHIAZOLES

This is a divisional application of copending application Ser. No. 07/746,821 filed on Aug. 19, 1991, U.S. Pat. No. 5,179,207.

FIELD OF THE INVENTION

This invention belongs to the field of organic chemistry. More particularly, it relates to substituted 2-aminothiophenes, 2-aminothiazoles, and bathochromic azo colorants prepared therefrom.

BACKGROUND OF THE INVENTION

Various synthetic methods are available for preparing negatively substituted 2-aminothiophenes and 2-aminothiazoles, which are useful as intermediates for preparing azo dyes for textile fibers. (See, for example, Weaver and Shuttleworth, *Dyes and Pigments*, 3, 81–121 (1982).) Many of these procedures are complicated and laborious, with accompanying low yields. Often, the starting materials needed are not readily available and are expensive, thus rendering the desired negatively substituted 2-aminothiophenes and 2-aminothiazoles prohibitively expensive. Normally, to produce the most bathochromic colorants when diazotized and coupled, the 2-aminothiophenes must have negative groups in the 2,5-positions. These intermediate compounds are usually essentially colorless or are pale yellow in color as are the negatively substituted 2-aminothiazoles. Various colors from yellow to cyan can be produced by diazotizing and coupling the diazonium salts thus produced with appropriate couplers. It is very desirable to produce bathochromic blue shades and these are normally only possible when two very strongly electron withdrawing groups are in positions 2 and 5 of the intermediate thiophenes. None of these known intermediate negatively substituted 2-aminothiophenes or 2-aminothiazoles are useful as colorants.

It is known that 2-chloro-3-cyanomaleimide reacts with primary aromatic amines such as aniline to replace one of the hydrogens attached to the nitrogen, e.g. aniline reacts to give 2-anilino-3-cyanomaleimide. (Wiley et al., *J. Am. Chem. Soc.*, 80, 138528 (1958)).

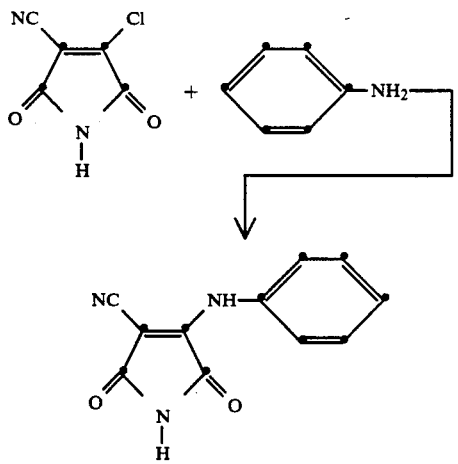

The compound thus produced has no significant color and has no utility as a colorant. Furthermore, since it has no primary amine present, the compound cannot be diazotized to produce a diazonium salt which is capable of being coupled to produce valuable azo colorants.

It is not expected, based on the prior art, that 2-aminothiophenes and 2-aminothiazoles, which contain primary amine groups, would react with 2-chloro-3-negatively substituted maleimides to give 5-negatively substituted 2-aminothiophenes and 2-aminothiazoles compounds useful as colorants and which have free primary amine groups capable of being diazotized to produce bathochromic azo dyes.

Various electron rich compounds are known to react with 2-chloro-3-cyanomaleimide to give colorants useful as colorants for textile fibers, but none have primary amine groups capable of being diazotized; no 2-aminothiophenes or 2-aminothiazoles are reacted. (See, for example, U.S. Pat. No. 3,096,339).

SUMMARY OF THE INVENTION

The present invention provides various substituted 2 aminothiazoles and thiophenes which are useful as intermediates in the synthesis of bathochromic azo dyes. These intermediates can then be diazotized and coupled with azo components, for example, anilines, 1,2,3,4-tetrahydroquinolines, 2,3-dihydroindoles, and 3,4-dihydro-2H-1,4-benzoxazines.

DETAILED DESCRIPTION OF THE INVENTION

The present invention provides compounds of Formula (I):

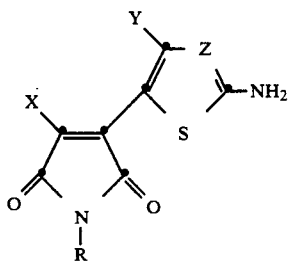

wherein

R is hydrogen, $C_1$–$C_8$ alkyl, $C_1$–$C_8$ substituted alkyl, $C_3$–$C_8$ alkenyl, $C_3$–$C_8$ alkynyl, $C_5$–$C_7$ cycloalkyl, $C_5$–$C_8$ substituted cycloalkyl, phenyl, or substituted phenyl;

X is cyano, $C_1$–$C_8$ alkylsulfonyl, phenylsulfonyl, or substituted phenylsulfonyl;

Y is hydrogen, $C_1$–$C_4$ alkyl, $C_5$–$C_7$ cycloalkyl, halogen, phenyl, substituted phenyl, 2-thienyl, 2-thienyl substituted with one or two halogen, $C_1$–$C_4$ alkyl, or $C_1$–$C_4$ alkoxy, or Y is 2-furanyl;

Z is nitrogen or a group of the formula $-C(R_1)=$, wherein $R_1$ is cyano, $-CO_2R_2$, $-COR_3$, $-CONHR_2$, or $-SO_2R_3$, wherein $R_2$ is hydrogen, $C_1$–$C_8$ alkyl, $C_1$–$C_8$ substituted alkyl, $C_5$–$C_7$ cycloalkyl, $C_3$–$C_8$ alkenyl, phenyl, or substituted phenyl, and $R_3$ is $C_1$–$C_8$ alkyl, phenyl, or substituted phenyl.

The utility of negatively substituted 2-amino thiazoles and 2-aminothiophenes for producing bathochromic azo dyes by diazotization and coupling of the diazonium salts thus produced with aromatic amines is known, but preparation of the intermediate amines requires complicated, laborious and expensive synthetic methods. In many cases the yields are low and multisteps synthetic routes are involved. (See, for example, John Griffiths, *Colour and Constitution of Organic Molecules,* Academic Press, London, 1976, p. 186; John Griffiths, editor, *Development in the Chemistry and Technology of Organic Dyes,* Blackwell Scientific Publications, Oxford, 1984, pages 11–13; and P. F. Gordon and P. Gregory, *Organic Chemistry in Colour,* Springer-Verlag, New York, 1983, page 130.)

In contrast, the negatively substituted 2-aminothiazoles and 2-aminothiophenes of this invention are prepared in high yields and in a one step reaction by reacting readily available 2-aminothiazoles and 2-aminothiophenes with maleimide compounds which contain as substitutents a reactive halogen in the 2-position and a negative groups, e.g., cyano, in the 3-position. For example, the available 2-aminothiazoles and 2-aminothiophenes of Formula (II) are reacted with 2-chloro-3-cyanomaleimide according to the following scheme:

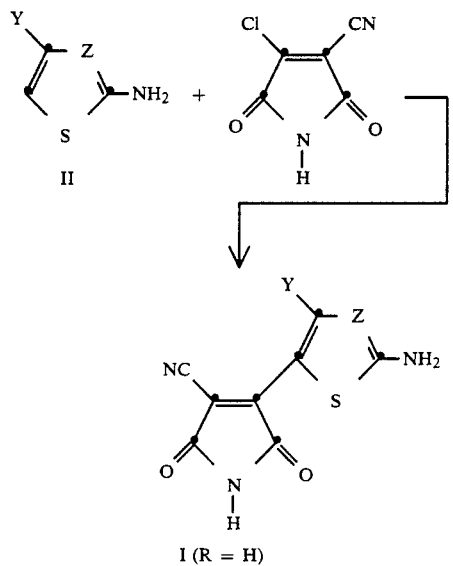

Inert solvents such as esters, e.g., ethyl acetate; halogenated hydrocarbons, e.g., methylene chloride; ketones, e.g., acetone and carboxamides, e.g., N,N-dimethylformamide may be used. The reaction temperatures typically vary between room temperature and about 100° C.

In another synthetic route, (E. L. Martin et al., *J. Org. Chem.,* 26, 2032 (1961), 2,3-dichloromaleimides are reacted with the intermediate 2-aminothiazoles and 2-aminothiophenes in the presence of metal cyanides, e.g., sodium cyanide or metal sulfinates, e.g., p-toluenesulfinic acid, Na salt to give compounds of Formula I.

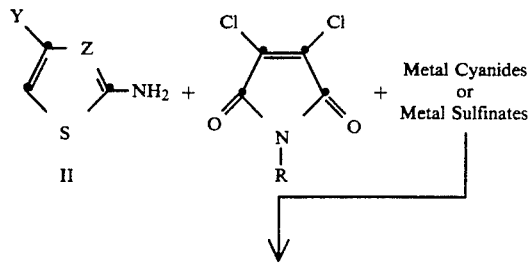

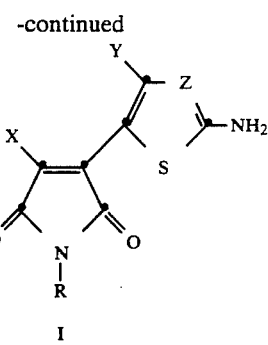

Compounds of Formula I may be used to color textile fibers red shades, but their primary utility is to provide bathochromic blue→cyan azo colorants III upon diazotization and coupling with azo components (C) selected from anilines, 1,2,3,4-tetrahydroquinolines, 2,3-dihydroindoles

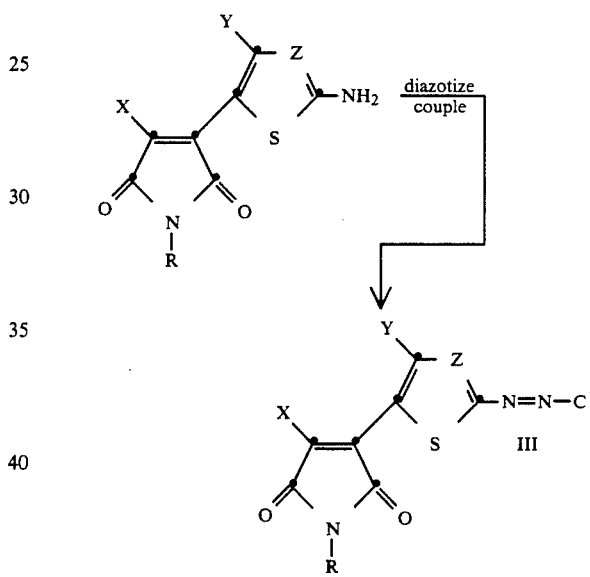

and 3,4-dihydro-2H-1,4-benzoxazines (benzomorpholines). Thus, as a further aspect of the present invention there is provided compounds of Formula (III). Especially preferred are those compounds where C is selected from the following formulae:

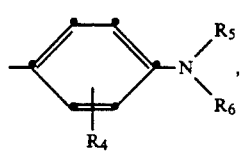

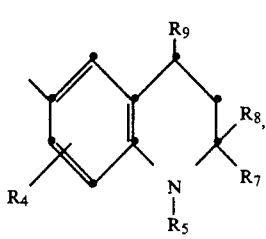

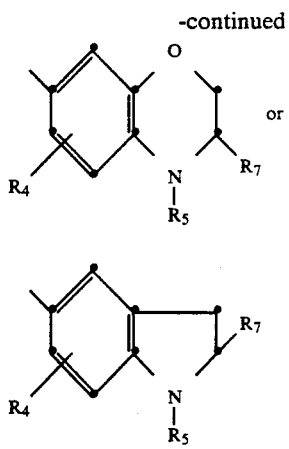

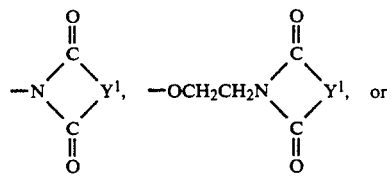

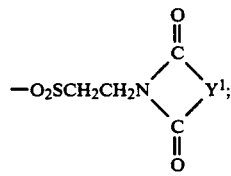

wherein:
R$_4$ is hydrogen or 1-2 groups selected from C$_1$-C$_4$ alkyl, C$_1$-C$_4$ alkoxy, halogen, NHCOR$_2$, NHSO$_2$R$_3$, NHCO$_2$R$_3$ or NHCONHR$_2$, wherein R$_2$ and R$_3$ are as defined previously;

R$_5$ and R$_6$ are selected from hydrogen, unsubstituted and substituted C$_1$-C$_8$ alkyl, C$_3$-C$_8$ alkenyl, C$_3$-C$_8$ alkynyl, unsubstituted and substituted C$_5$-C$_7$ cycloalkyl and unsubstituted and substituted phenyl. Also, R$_5$ and R$_6$ may be combined with the nitrogen to which they are attached to form a radical having the formula

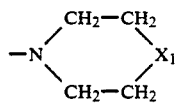

wherein
X$_1$ is selected from —CH$_2$—, —O—, —S—, —SO$_2$—, —CO—, —CO$_2$—, —NH—, —N—COC$_1$-C$_4$ alkyl or —N—SO$_2$C$_1$-C$_4$ alkyl.

R$_7$, R$_8$ and R are hydrogen or C$_1$-C$_4$ alkyl.

The C$_1$-C$_8$ unsubstituted are substituted alkyl groups represented by R, R$_2$ and R$_3$ include straight or branched chain fully saturated hydrocarbon radicals and these substituted with at least one substituent selected from halogen, hydroxy, C$_1$-C$_6$ alkoxy, C$_1$-C$_6$ alkanoyloxy, C$_5$-C$_7$ cycloalkyl, cyano, C$_1$-C$_6$ carbalkoxy, phenyl or substituted phenyl and phenoxy or substituted phenoxy.

The C$_1$-C$_8$ unsubstituted and substituted alkyl groups represented by R$_5$ and R$_6$ include straight or branched chain fully saturated hydrocarbon radicals and these substituted with one or more of the following: C$_5$-C$_7$ cycloalkyl and C$_5$-C$_7$ cycloalkyl substituted with one or two of C$_1$-C$_6$ alkyl, C$_1$-C$_6$ alkoxy or halogen; phenyl and phenyl substituted with one or two of C$_1$-C$_6$ alkyl, C$_1$-C$_6$ alkoxy, C$_1$-C$_6$ alkoxycarbonyl, halogen, C$_1$-C$_6$ alkanoylamino, cyano, nitro or C$_1$-C$_6$ alkylsulfonyl; cyano; hydroxy; halogen; 2-pyrrolidino; phthalimidino; vinylsulfonyl; acrylamido; o-benzoic sulfimido; C$_1$-C$_6$ alkoxy; C$_1$-C$_6$ alkoxy-C$_1$-C$_6$ alkoxy; cyano C$_1$-C$_6$ alkoxy; hydroxy C$_1$-C$_6$ alkoxy; phenoxy; phenoxy substituted with C$_1$-C$_6$ alkyl, C$_1$-C$_6$ alkoxy, or halogen; groups of the formulae:

wherein
Y$^1$ is selected from o-phenylene; o-phenylene substituted with C$_1$-C$_6$ alkyl, C$_1$-C$_6$ alkoxy, halogen or nitro; C$_2$-C$_3$ alkylene; —O—CH$_2$—; —OCH$_2$CH$_2$—; —CH$_2$OCH$_2$—; —S—CH$_2$—; —CH$_2$SCH$_2$—; —NHCH$_2$—; —NHCH$_2$CH$_2$—; —N(alkyl)CH$_2$—; —N(alkyl)CH$_2$CH$_2$— or —NHC(C$_6$H$_5$)$_2$—; groups of the formulae:

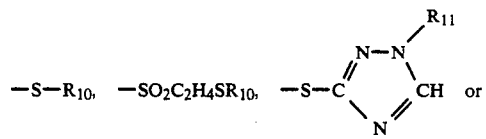

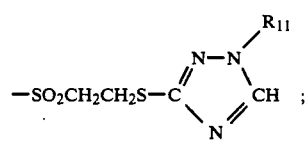

wherein
R$_{10}$ is selected from C$_1$-C$_6$ alkyl; C$_5$-C$_7$ cycloalkyl; phenyl; phenyl substituted with one or more groups selected from C$_1$-C$_6$ alkyl, C$_1$-C$_6$ alkoxy or halogen; pyridyl, pyrimidinyl; benzoxazolyl; benzothiazolyl; benzimidazolyl; 1,3,4-thiadiazolyl, 1,3,4-oxadiazolyl; these heterocyclic radicals substituted with one or more groups selected from C$_1$-C$_6$ alkyl, C$_1$-C$_6$ alkoxy or halogen; wherein R$_{11}$ is selected from hydrogen, lower alkyl or benzyl; groups of the formulae:

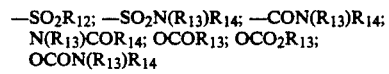

wherein
R$_{12}$ is selected from C$_5$-C$_7$ cycloalkyl; C$_5$-C$_7$ cycloalkyl substituted with C$_1$-C$_6$ alkyl; allyl; phenyl; phenyl substituted with one or two groups selected from C$_1$-C$_6$ alkyl, C$_1$-C$_6$ alkoxy or halogen; C$_1$-C$_6$ alkyl; C$_1$-C$_6$ alkyl substituted with one or more groups selected from C$_1$-C$_6$ alkoxy, halogen, cyano, C$_5$-C$_7$ cycloalkyl, phenyl, phenoxy, C$_1$-C$_6$ alkylthio or C$_1$-C$_6$ alkylsulfonyl; R$_{13}$ and R$_{14}$ are each independently selected from hydrogen or those groups represented by R$_{12}$.

In the terms C$_1$-C$_6$ alkyl, C$_1$-C$_6$ alkoxy, C$_1$-C$_6$ alkanoyloxy, C$_1$-C$_6$ alkoxycarbonyl, C$_1$-C$_6$ alkylsulfonyl, and C$_1$-C$_6$ alkylthio, the alkyl portion of the moiety is a fully saturated straight or branched chain hydrocarbon radical having from one to six carbons.

The unsubstituted and substituted $C_5$-$C_7$ cycloalkyl groups mentioned above refer to cycloaliphatic hydrocarbon groups which contain 5 to 7 carbons in the ring and these cycloalkyl groups substituted with one or two of $C_1$-$C_4$ alkyl, $C_1$-$C_4$ alkoxy, hydroxy or $C_1$-$C_4$ alkanoyloxy.

The substituted phenyl groups mentioned above, unless otherwise specified, represent such phenyl groups substituted by one or two of $C_1$-$C_6$ alkyl, $C_1$-$C_6$ alkoxy, $C_1$-$C_6$ alkoxycarbonyl, $C_1$-$C_6$ alkanoyloxy, $C_1$-$C_6$ alkanoylamino, halogen, cyano, $C_1$-$C_6$ alkylsulfonyl or hydroxy.

The term $C_3$-$C_8$ alkenyl is used to represent straight or branched chain hydrocarbon radical which contains three to eight carbons and at least one carbon-carbon double bond, e.g., allyl, while the term $C_3$-$C_8$ alkynyl refers to a straight or branched chain hydrocarbon carbon radical which contains three to eight carbons and at least one carbon-carbon triple bond.

The preferred compounds of Formula I are those wherein R is hydrogen; X is cyano; Y is selected from hydrogen, methyl, 2-thienyl, phenyl and phenyl substituted with $C_1$-$C_4$ alkyl, $C_1$-$C_4$ alkoxy or halogen; Z is selected from —C(CN)=, —C(CO$_2$C$_1$-C$_4$ alkyl)=, and N=. The —C(COC$_6$H$_5$)=, —C(SO$_2$C$_6$H$_5$)=, —C(SO$_2$C$_1$-C$_4$ alkyl)= and —N=. The preferred colorants are derived by diazotizing these preferred compounds of Formula I and coupling the thus produced diazonium salts with aromatic amine couplers to produce colorants III, wherein $R_4$ is selected from hydrogen, methyl, halogen, $C_1$-$C_4$ alkoxy and NHCOC$_1$-$C_4$ alkyl; $R_5$ and $R_6$ are selected from $C_1$-$C_4$ alkyl and $C_1$-$C_4$ alkyl substituted with hydroxy, $C_1$-$C_4$ alkoxy, $C_1$-$C_4$ alkoxy-$C_1$-$C_4$ alkoxy, cyano, carbamyl, NHCOC$_1$-$C_4$ alkyl, SO$_2$C$_1$-$C_4$ alkyl, phenyl, cyclohexyl, $C_1$-$C_4$ alkanoyloxy, $C_1$-$C_4$ alkoxycarbonyl, succinimido; cyclohexyl; allyl; $R_7$, $R_8$ and $R_9$ are hydrogen or methyl.

EXPERIMENTAL SECTION

Example 1

Preparation of 2-amino-3-carbomethoxy-5-(3-cyanomaleimid-2-yl)thiophene

A solution of 2-chloro-3-cyanomaleimide (0.4 g, 0.0025 m) in ethyl acetate (15 mL) was mixed with a solution of 2-amino-3-carbomethoxythiophene (0.5 g, 0.0025 m) dissolved in ethyl acetate (20 mL) and the reaction mixture stirred for 2 hours. The crystalline dark red colorant thus produced was collected by filtration, washed with ethyl acetate and dried in air (yield 0.5 g, 72% of the theoretical yield). Mass spectrometry supports the following structure:

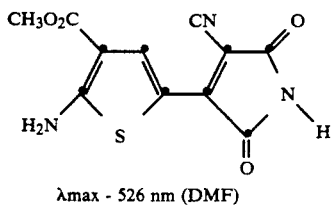

λmax - 526 nm (DMF)

The colorant has an absorption maximum (λmax) at 526 nm and an extinction coefficient of 17,577 in N,N-dimethylformamide (DMF) solution.

Example 2

To 2-amino-3-carbomethoxy-4-methylthiophene (0.43 g, 0.0025 m) stirred in ethyl acetate (15 mL) was added 2-chloro-3-cyanomaleimide (0.40 g, 0.0026 m) and the reaction mixture heated at reflux for 1.0 hour. The colorant thus produced was collected by filtration, washed with ethyl acetate and dried in air (yield-0.56 g, 76.7% of the theoretical yield). Mass spectrometry supports the following structure:

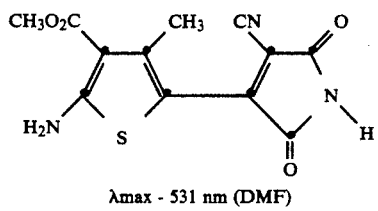

λmax - 531 nm (DMF)

In the visible absorption spectrum in N,N-dimethyl formamide (DMF) an absorption maximum is observed at 531 nm. The colorant has an extinction coefficient of 20,523.

Example 3

2-amino-3-cyano-4-methylthiophene (0.69 g, 0.005 m) and 2-chloro-3-cyanomaleimide (0.80 g, 0.0052 m) were reacted by mixing in ethyl acetate (15 mL) and heating the reaction mixture at reflux for 5 minutes, followed by stirring for one hour while allowing to cool to room temperature. The crystalline product thus produced was collected by filtration, washed with ethyl acetate and dried in air (yield-1.25 g, 96.9% of the theoretical yield). Mass spectrometry supports the following structure:

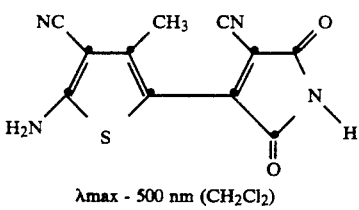

λmax - 500 nm (CH$_2$Cl$_2$)

The colorant when dissolved in CH$_2$Cl$_2$ has an absorption maximum at 500 nm and an extinction coefficient (e) of 19,061.

Example 4

To 2-amino-3-phenylsulfonylthiophene (1.03 g, 0.005 m) stirred at room temperature in ethyl acetate (20 mL) was added 2-chloro-3-cyanomaleimide (0.78 g, 0.005 m) and the reaction mixture heated at 90°-95° C. for 0.5 hour and allowed to cool. The product was collected by filtration, washed with ethyl acetate and dried in air (yield-1.1 g, 61% of the theoretical yield). Mass spectrometry supports the following structure:

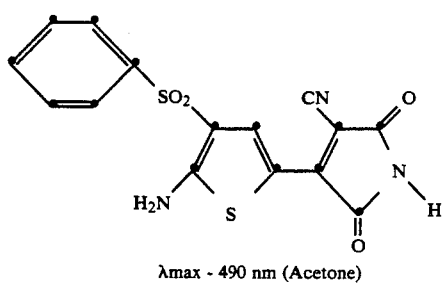

λmax - 490 nm (Acetone)

In acetone, a visible absorption maximum is observed at 490 nm ($\epsilon=26,773$) in the visible absorption spectrum.

Example 5

To 2-amino-4-phenylthiazole (3.52 g, 0.02 m) stirred in ethyl acetate (50.0 mL) was added 2-chloro-3-cyanomaleimide (3.12 g, 0.03 m) and the reaction mixture heated at reflux for about 5 minutes and then allowed to cool. The product was collected by filtration, washed with ethyl acetate and dried in air (yield-5.0 g). Mass spectrometry supports the following structure:

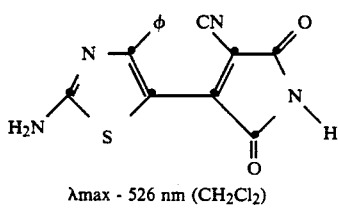

λmax - 526 nm (CH$_2$Cl$_2$)

An absorption maximum at 526 nm ($\epsilon=4,379$) is observed in the visible absorption spectrum in methylene chloride.

Example 6

A solution of the dichloromaleimide compound (1.57 g, 0.005)m having the structure:

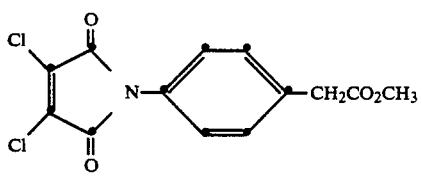

dissolved in N,N-dimethylformamide (10 mL) was treated with 2-amino-3-carbomethoxy-4-methylthiophene (0.86 g, 0.005 m) and then with p toluenesulfinic acid, sodium salt (1.0 g, 0.0056 m) and the reaction mixture stirred at room temperature for 10 minutes and then drowned into water (100 mL) with stirring. The solid product thus produced was collected by filtration, washed with water and dried in air (yield-2.3 g, 80.9% of the theoretical yield). Mass spectrometry supports the following structure:

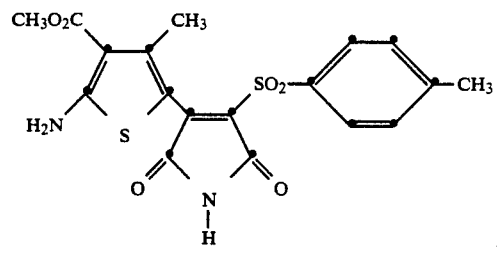

λmax - 537 nm (CH$_2$Cl$_2$)

An absorption maximum is observed at 537 nm ($\epsilon_{max}=6,422$) in the visible absorption spectrum in methylene chloride.

Example 7

The dichloromaleimide compound (2.36 g, 0.01 m) having the structure:

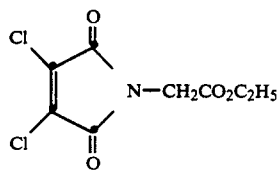

dissolved in 15 mL of acetic acid was reacted with 2-amino-3-carbomethoxy-4-methylthiophene (1.71 g, 0.01 m) and p-toluenesulfinic acid, sodium salt (2.0 g) by stirring the reaction mixture at room temperature for 30 minutes. Isopropanol (50 mL) and then water (100 mL) are added gradually to the reaction mixture with stirring. The product, which is initially oily, crystallizes upon standing for several hours at room temperature and is collected by filtration, washed with water and dried in air (yield-2.9 g, 57.3% of the theoretical yield). Mass spectrometry supports the following proposed structure:

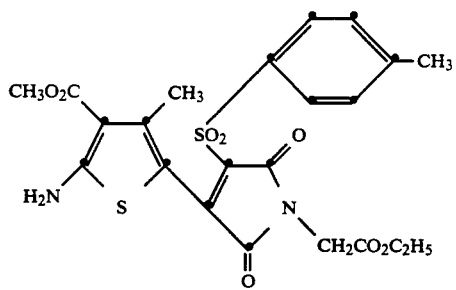

λmax - 533 nm (CH$_2$Cl$_2$)

An absorption maximum is observed at 533 nm ($\epsilon_{max}=9,459$) in the visible absorption spectrum in methylene chloride.

Examples 8 and 9

Diazotization and Coupling

To concentrated sulfuric acid (5.0 mL) was added dry sodium nitrite (0.72 g) portionwise with stirring, while allowing the temperature to rise. After cooling, 1:5 acid (1 part propionic acid: 5 parts acetic acid, v/v) (10 mL) was added at below 5° C. After further cooling, the amine compound of Example 3 (2.58 g, 0.01 m) was added portionwise with good stirring, followed by an additional 15 mL of 1:5 acid, both added at 0.5° C. The reaction mixture was then stirred at 0.5° C. for 2.0 hours. A 0.005 m portion of the diazonium salt solution was added to a chilled solution of 0.005 m of each of the following couplers dissolved in 25 mL of 1:5 acid:

Example 8

3-acetamido-N,N-diethylaniline

Example 9

N-ethyl-7-propionamido-1,2,3,4-tetrahydro-2,2,4-trimethylquinoline

Ammonium acetate was added to each of the above coupling mixtures with stirring until they were neutral to Congo Red test paper. After being allowed to couple for 0.5 hour, the blue colorants were precipitated by the addition of water, collected by filtration, washed with water and dried in air. The yield of the colorant of Example 8 was 2.0 g (84.9% of the theoretical yield) and the yield of colorant of Example 9 was 2.2 g (81.4% of the theoretical yield). Each compound was reslurried twice in hot methanol (25 mL), followed by cooling, filtering, washing with methanol and finally drying in air. Mass spectrometry supports the following structures:

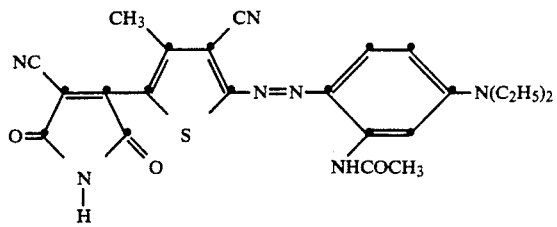

Example 8

λmax - 603 nm (DMF)

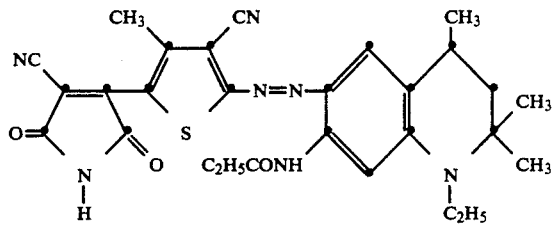

Example 9

λmax - 625 nm (DMF)

In the visible spectra in N,N-dimethylformamide (DMF), the colorant of Example 8 has an absorption maximum (λmax) at 603 nm ($\epsilon_{max}$—41,188), while the colorant of Example 9 has an absorption maximum at 625 nm ($\epsilon_{max}$—48,038). Tables 1-3 illustrate further the scope of the invention.

TABLE 1

COMPOUNDS OF FORMULA I

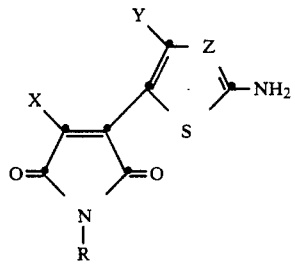

| Ex. No. | R | X | Y | Z |
|---|---|---|---|---|
| 10 | H | CN | H | —C(CN)= |
| 11 | H | CN | $C_2H_5$ | —C(CN)= |
| 12 | H | CN | $C_6H_4$-4-$CH_3$ | —C(CN)= |
| 13 | H | CN | $CH_3$ | —C(CONH$_2$)= |
| 14 | H | CN | H | —C(CONHCH$_3$)= |
| 15 | H | CN | H | —C(CONHC$_4$H$_9$-n)= |
| 16 | H | CN | $CH_3$ | —C(CONHC$_3$H$_6$OCH$_3$)= |
| 17 | H | CN | $CH_3$ | —C(CONHC$_2$H$_4$OH)= |
| 18 | H | CN | $CH_3$ | —C(CONHC$_6$H$_{11}$)= |
| 19 | H | CN | H | —C(CONHCH$_2$CH=CH$_2$)= |
| 20 | H | CN | $CH_3$ | —C(CONHC$_6$H$_5$)= |
| 21 | H | CN | $CH_3$ | —C(SO$_2$C$_6$H$_5$)= |
| 22 | H | CN | H | —C(CO$_2$C$_2$H$_4$OC$_2$H$_5$)= |
| 23 | H | CN | H | —C(CO$_2$C$_5$H$_9$)= |
| 24 | H | CN | $C_6H_4$-4-OCH$_3$ | —C(CO$_2$C$_2$H$_4$OCOCH$_3$)= |
| 25 | H | CN | $C_6H_4$-4-Cl | —C(CO$_2$CH$_2$CH=CH$_2$)= |
| 26 | H | CN | $C_6H_{11}$ | —C(CO$_2$CH$_2$CH$_2$C$_6$H$_5$)= |
| 27 | H | CN | $C_6H_{10}$-p-CH$_3$ | —C(CO$_2$CH$_2$CH$_2$OC$_6$H$_5$)= |
| 28 | H | CN | $C_6H_3$-3,4-diCl | —C(CO$_2$C$_6$H$_5$)= |
| 29 | H | SO$_2$C$_6$H$_5$ | $CH_3$ | —C(CN)= |
| 30 | H | SO$_2$CH$_3$ | H | —C(CO$_2$CH$_3$)= |
| 31 | H | SO$_2$C$_4$H$_9$-n | $C_6H_5$ | —C(CN)= |
| 32 | H | SO$_2$C$_6$H$_3$-3,4-diCl | H | —C(CN)= |
| 33 | H | SO$_2$C$_6$H$_{11}$ | $CH_3$ | —C(CONHC$_2$H$_5$)= |
| 34 | $C_2H_5$ | CN | H | —C(CN)= |
| 35 | $C_6H_5$ | CN | $CH_3$ | —C(CN)= |
| 36 | CH$_2$CH=CH$_2$ | CN | Cl | —C(CN)= |
| 37 | CH$_2$C$_6$H$_5$ | CN | Br | —C(SO$_2$CH$_3$)= |
| 38 | CH$_2$CH$_2$OH | CN | H | —C(CO$_2$C$_2$H$_5$)= |

TABLE 1-continued

COMPOUNDS OF FORMULA I

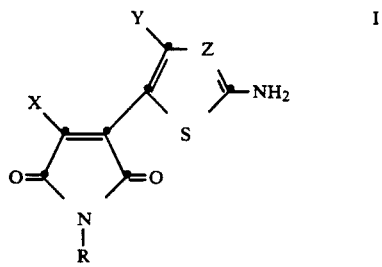

| Ex. No. | R | X | Y | Z |
|---|---|---|---|---|
| 39 | H | CN | H | $-C(CO_2C_8H_{17}\text{-n})=$ |
| 40 | H | CN | 2-thienyl | $-C(CN)=$ |
| 41 | H | CN | 5-chloro-2-thienyl | $-C(CO_2CH_3)=$ |
| 42 | H | CN | 2-furyl | $-C(CN)=$ |
| 43 | H | CN | 5-methyl-2-thienyl | $-C(CO_2C_2H_5)=$ |
| 44 | H | CN | H | $-N=$ |
| 45 | H | CN | $CH_3$ | $-N=$ |
| 46 | $CH_3$ | CN | $C_6H_5$ | $-N=$ |
| 47 | $C_6H_{11}$ | CN | $C_6H_4\text{-4-}OC_2H_5$ | $-N=$ |
| 48 | $CH_2CH_2C_6H_5$ | $SO_2C_6H_5$ | $C_6H_5$ | $-N=$ |
| 49 | H | $SO_2C_6H_4\text{-4-Cl}$ | $C_6H_4\text{-4-Cl}$ | $-N=$ |
| 50 | H | $SO_2C_6H_4\text{-2-Br}$ | $C_6H_4\text{-2-Br}$ | $-N=$ |
| 51 | H | CN | thienyl | $-N=$ |
| 52 | H | CN | 5-bromo-2-thienyl | $-N=$ |
| 53 | H | CN | furyl | $-N=$ |
| 54 | H | CN | 5-methyl-2-thienyl | $-N=$ |
| 55 | H | CN | $-C_6H_4\text{-4-}C_4H_9\text{-n}$ | $-N=$ |
| 56 | H | CN | $-C_6H_4\text{-4-CHCOCH}_3$ | $-N=$ |
| 57 | $C_6H_4\text{-4-}CO_2CH_3$ | $SO_2C_6H_5$ | $-C_6H_4\text{-2-}OC_4H_9\text{-n}$ | $-N=$ |
| 58 | $C_6H_4\text{-4-}SO_2CH_3$ | $SO_2C_6H_4\text{-4-}CH_3$ | $-C_6H_4\text{-4-OH}$ | $-N=$ |
| 59 | H | CN | $-C_6H_4\text{-4-}OCOCH_3$ | $-N=$ |
| 60 | $CH_2C_6H_4\text{-3-CN}$ | CN | $C_6H_5$ | $-N=$ |
| 61 | H | CN | $CH_3$ | $-C[CO_2CH(CH_3)_2]=$ |
| 62 | H | CN | $CH_3$ | $-C[CO_2CH_2CH(C_2H_5)C_4H_9\text{n}]=$ |
| 63 | H | CN | H | $-C[CO_2C_2H_4OC_2H_4OH]=$ |
| 64 | H | CN | H | $-C[CO_2CH(CH_3)]C_2H_5=$ |
| 65 | H | CN | H | $-C(COC_6H_5)=$ |
| 66 | H | CN | H | $-C[COC(CH_3)_3]=$ |

TABLE 2

COLORANTS OF FORMULA III

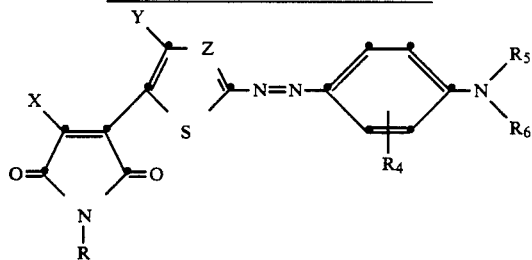

| Ex. No. | R | X | Y | Z |
|---|---|---|---|---|
| 67 | H | CN | H | $-C(CN)=$ |
| 68 | H | CN | H | $-C(CO_2CH_3)=$ |
| 69 | H | CN | $CH_3$ | $-C(CN)=$ |
| 70 | H | CN | $CH_3$ | $-C(CN)=$ |
| 71 | H | CN | H | $-C(CO_2C_2H_5)=$ |
| 72 | H | CN | H | $-C(CO_2C_4H_9\text{-n})=$ |
| 73 | H | CN | H | $-C(CO_2C_6H_{11})=$ |
| 74 | H | CN | $C_6H_5$ | $-C(CN)=$ |
| 75 | H | CN | $CH_3$ | $-C(SO_2C_6H_5)=$ |
| 76 | H | CN | H | $-C(SO_2C_6H_5)=$ |
| 77 | H | CN | H | $-C(CO_2CH_3)=$ |
| 78 | H | CN | H | $-C(CO_2CH_3)=$ |
| 79 | H | CN | H | $-C(CO_2CH_3)=$ |
| 80 | H | CN | H | $-C(COC_6H_5)=$ |
| 81 | H | CN | H | $-C[COC(CH_3)_3]=$ |
| 82 | H | CN | H | $-C(CO_2C_2H_5)=$ |
| 83 | H | CN | H | $-C(CN)=$ |
| 84 | H | CN | H | $-C(CN)=$ |

TABLE 2-continued

| | | | | |
|---|---|---|---|---|
| 85 | H | CN | H | —C(CN)= |
| 86 | H | CN | H | —C(CO$_2$CH$_3$)= |
| 87 | H | CN | CH$_3$ | —C(SO$_2$C$_6$H$_5$)= |
| 88 | H | CN | CH$_3$ | —C(SO$_2$CH$_3$)= |
| 89 | H | CN | H | —C(CO$_2$CH$_3$)= |
| 90 | H | CN | 2-thienyl | —C(CN)= |
| 91 | H | CN | 2-furyl | —C(CN)= |
| 92 | C$_6$H$_5$ | SO$_2$C$_6$H$_5$ | CH$_3$ | —C(CN)= |
| 93 | C$_6$H$_4$-4-CH$_2$CO$_2$CH$_3$ | SO$_2$C$_6$H$_4$-4-CH$_3$ | CH$_3$ | —C(CO$_2$CH$_3$)= |
| 94 | CH$_2$CO$_2$C$_2$H$_5$ | SO$_2$C$_6$H$_4$-4-CH$_3$ | CH$_3$ | —C(CO$_2$CH$_3$)= |
| 95 | C$_2$H$_5$ | CN | H | —C(CN)= |
| 96 | C$_2$H$_5$ | CN | H | —N= |
| 97 | H | CN | CH$_3$ | —N= |
| 98 | H | CN | C$_6$H$_5$ | —N= |
| 99 | H | CN | C$_6$H$_5$ | —N= |
| 100 | H | CN | C$_6$H$_5$ | —N= |
| 101 | H | CN | C$_6$H$_5$ | —N= |
| 102 | H | CN | C$_6$H$_5$ | —N= |
| 103 | H | CN | C$_6$H$_5$ | —N= |
| 104 | H | CN | C$_6$H$_5$ | —N= |
| 105 | H | CN | 2-thienyl | —N= |
| 106 | H | CN | 2-furyl | —N= |
| 107 | H | CN | 5-bromo-2-furyl | —N= |
| 108 | H | SO$_2$C$_6$H$_5$ | C$_6$H$_5$ | —N= |
| 109 | CH$_2$CO$_2$C$_2$H$_5$ | SO$_2$C$_6$H$_4$-4-CH$_3$ | C$_6$H$_5$ | —N= |
| 110 | C$_6$H$_{11}$ | CN | C$_6$H$_5$ | —N= |
| 111 | H | CN | C$_6$H$_4$-4-CH$_3$ | —N= |
| 112 | H | CN | C$_6$H$_4$-4-OCH$_3$ | —N= |
| 113 | H | CN | C$_6$H$_4$-4-Cl | —N= |
| 114 | H | CN | C$_6$H$_5$ | —N= |
| 115 | H | CN | C$_6$H$_5$ | —N= |
| 116 | H | CN | C$_6$H$_{11}$ | —N= |
| 117 | H | CN | C(CH$_3$)$_3$ | —N= |
| 118 | H | CN | C$_6$H$_5$ | —N= |
| 119 | H | CN | C$_6$H$_5$ | —N= |
| 120 | H | CN | C$_6$H$_5$ | —N= |
| 121 | H | CN | C$_6$H$_5$ | —N= |
| 122 | H | CN | C$_6$H$_5$ | —N= |
| 123 | H | CN | C$_6$H$_5$ | —N= |

COLORANTS OF FORMULA III

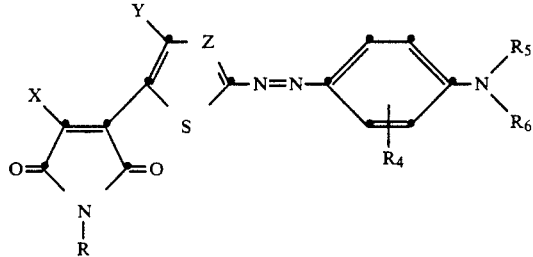

| Ex. No. | R$_4$ | R$_5$ | R$_6$ |
|---|---|---|---|
| 67 | H | C$_2$H$_5$ | C$_2$H$_5$ |
| 68 | 3-CH$_3$ | C$_2$H$_5$ | C$_2$H$_4$OH |
| 69 | 3-OCH$_3$ | C$_4$H$_9$-n | C$_4$H$_9$-n |
| 70 | 2-OCH$_3$-5-CH$_3$ | H | CH(CH$_3$)C$_2$H$_5$ |
| 71 | 3-Cl | CH$_2$CH$_2$OCOCH$_3$ | CH$_2$CH$_2$OCOCH$_3$ |
| 72 | 3-NHCOCH$_3$ | C$_3$H$_7$-n | C$_3$H$_7$-n |
| 73 | 3-NHCOC$_2$H$_5$ | C$_2$H$_5$ | CH$_2$C$_6$H$_5$ |
| 74 | 3-NHCO$_2$C$_2$H$_5$ | C$_2$H$_5$ | C$_6$H$_{11}$ |
| 75 | 3-NHCOC$_6$H$_5$ | C$_2$H$_5$ | CH$_2$CH$_2$OCOC$_2$H$_5$ |
| 76 | 3-NHCONHC$_6$H$_5$ | C$_2$H$_5$ | CH$_2$C$_6$H$_{11}$ |
| 77 | 2-OCH$_3$-5-NHCOCH$_3$ | C$_2$H$_5$ | C$_2$H$_5$ |
| 78 | 2,5-di-OCH$_3$ | H | C$_6$H$_{11}$ |
| 79 | 3-NHCOCH$_2$OH | C$_2$H$_5$ | C$_2$H$_5$ |
| 80 | 3-NHCOCH$_3$ | C$_2$H$_5$ | C$_6$H$_{11}$ |
| 81 | 3-NHCOCH$_3$ | C$_2$H$_5$ | CH$_2$CH$_2$CN |
| 82 | 3-CH$_3$ | C$_2$H$_4$OCOCH$_3$ | C$_2$H$_4$OCOCH$_3$ |
| 83 | 3-NHCOCH$_3$ | —C$_2$H$_4$OC$_2$H$_4$— | |
| 84 | H | —C$_2$H$_4$SO$_2$C$_2$H$_4$— | |
| 85 | 3-CH$_3$ | —C$_2$H$_4$N(COCH$_3$)C$_2$H$_4$— | |
| 86 | H | —C$_2$H$_4$SC$_2$H$_4$— | |
| 87 | 3-NHSO$_2$CH$_3$ | C$_2$H$_5$ | C$_2$H$_5$ |
| 88 | 3-NHSO$_2$C$_6$H$_5$ | C$_3$H$_7$-n | C$_3$H$_7$-n |
| 89 | 3-NHCOCH$_3$ | C$_2$H$_5$ | CH$_2$CH(OH)CH$_2$OH |
| 90 | 3-NHCOCH$_3$ | C$_2$H$_5$ | CH$_2$CH$_2$OCH$_2$CH$_2$OC$_2$H$_5$ |
| 91 | 3-NHCOC$_6$H$_{11}$ | C$_4$H$_9$-n | CH$_2$CH$_2$OCH$_2$CH$_2$OH |
| 92 | 3-NHCOCH(CH$_3$)$_2$ | C$_2$H$_5$ | CH$_2$CH(OCOCH$_3$)CH$_2$OCOCH$_3$ |
| 93 | 3-NHCOC$_2$H$_5$ | C$_2$H$_5$ | CH$_2$CH$_2$C$_6$H$_5$ |

TABLE 2-continued

| | | | |
|---|---|---|---|
| 94 | 2-OCH₃-5-NHCOC₂H₅ | H | C₆H₁₁ |
| 95 | 3-NHCOH | C₈H₁₇-n | C₈H₁₇-n |
| 96 | 3-NHCOCH₃ | C₃H₇-n | C₃H₇-n |
| 97 | 3-NHCOCH₃ | C₂H₅ | 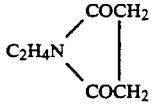 |
| 98 | 3-NHCOC₂H₅ | C₂H₅ | 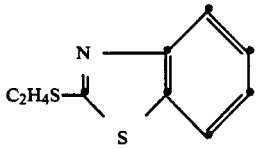 |
| 99 | 3-CH₃ | C₂H₅ | 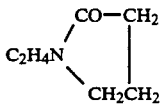 |
| 100 | 3-CH₃ | C₂H₅ | C₂H₄OCONHC₆H₅ |
| 101 | 3-CH₃ | C₂H₅ | C₃H₆NHCOCH₃ |
| 102 | H | C₂H₅ | CH₂CH₂CONH₂ |
| 103 | 3-NHCOCH₃ | C₂H₅ | CH₂CH₂SC₆H₅ |
| 104 | 3-NHCOC₂H₅ | C₂H₅ | CH₂CH₂SC₄H₉-n |
| 105 | 3-CH₃ | C₂H₅ | CH₂CH₂CO₂C₂H₅ |
| 106 | 3-CH₃ | C₂H₅ | CH₂CH₂Cl |
| 107 | 3-CH₃ | C₂H₅ | CH₂CH₂CN |
| 108 | 2-Cl | H | CH₂CH₂OH |
| 109 | 2-CH₃ | H | C₂H₅ |
| 110 | 2-Cl-5-OCH₃ | CH₂CH₂OH | CH₂CH₂OH |
| 111 | 3-CH₃ | C₂H₅ | CH₂CH₂NHSO₂CH₃ |
| 112 | 3-CH₃ | CH₂CH₂OCO₂C₂H₅ | CH₂CH₂OCO₂C₂H₅ |
| 113 | 3-CH₃ | C₄H₉-n | CH₂CH₂Cl |
| 114 | 3-NHCOCH₃ | C₂H₅ | CH₂CH(OH)CH₂OH |
| 115 | H | C₂H₅ | CH₂C₆H₄-4-CO₂CH₃ |
| 116 | H | C₂H₅ | 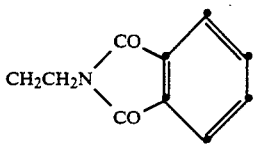 |
| 117 | 3-CH₃ | C₂H₅ | 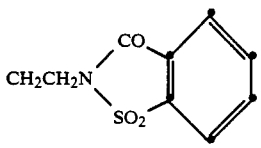 |
| 118 | 3-CH₃ | C₂H₅ | 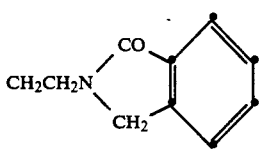 |
| 119 | 3-C₂H₅ | C₂H₅ | 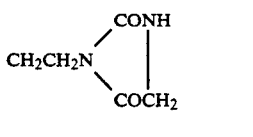 |
| 120 | H | C₂H₅ | 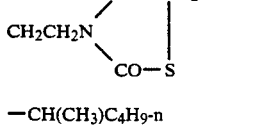 |
| 121 | 3-NHCOCH₃ | H | —CH(CH₃)C₄H₉-n |
| 122 | 3-CH₃ | C₂H₅ | CH₂CH(OH)CH₂Cl |

TABLE 2-continued

| 123 | 3-CH$_3$ | C$_2$H$_5$ | 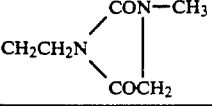 |

TABLE 3

COLORANTS OF FORMULA III

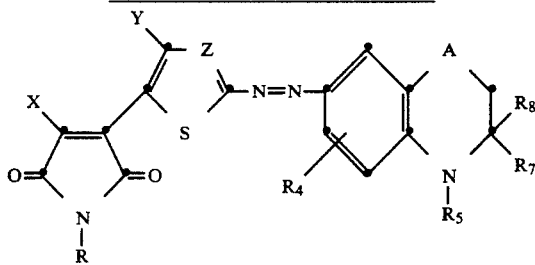

| Ex. No. | R | X | Y | Z | R$_4$ |
| --- | --- | --- | --- | --- | --- |
| 124 | H | CN | H | —C(CN)= | 7-NHCOCH$_3$ |
| 125 | H | CN | H | —C(CN)= | 7-CH$_3$ |
| 126 | H | CN | H | —C(CN)= | H |
| 127 | H | CN | H | —C(CN)= | 7-CH$_3$ |
| 128 | H | CN | H | —C(CO$_2$CH$_3$)= | 7-NHCOC$_2$H$_5$ |
| 129 | H | CN | CH$_3$ | —C(CO$_2$C$_2$H$_5$)= | 7-CH$_3$ |
| 130 | H | CN | CH$_3$ | —C(CN)= | H |
| 131 | H | CN | CH$_3$ | —C(CN)= | 5-CH$_3$, 8-OCH$_3$ |
| 132 | H | CN | CH$_3$ | —C(CN)= | 7-CH$_3$ |
| 133 | H | CN | CH$_3$ | —C(CN)= | 7-OCH$_3$ |
| 134 | H | CN | CH$_3$ | —C(CN)= | 7-CH$_3$ |
| 135 | H | CN | CH$_3$ | —C(CN)= | 7-CH$_3$ |
| 136 | H | CN | CH$_3$ | —C(CN)= | 7-OC$_2$H$_5$ |
| 137 | H | CN | CH$_3$ | —C(CN)= | H |
| 138 | H | CN | CH$_3$ | —C(CN)= | H |
| 139 | H | CN | CH$_3$ | —C(CN)= | 7-CH$_3$ |
| 140 | H | CN | H | —C(CN)= | 7-NHCOCH$_3$ |
| 141 | H | CN | H | —C(CN)= | 7-NHCOC$_2$H$_5$ |
| 142 | H | CN | C$_6$H$_5$ | —N= | 7-NHCOCH$_3$ |
| 143 | H | CN | C$_6$H$_5$ | —N= | 7-CH$_3$ |
| 144 | H | CN | C$_6$H$_5$ | —N= | 7-NHCOCH$_3$ |
| 145 | H | CN | C$_6$H$_5$ | —N= | H |
| 146 | H | CN | C$_6$H$_5$ | —N= | 7-CH$_3$ |
| 147 | H | CN | H | —C(CN)= | 7-NHCOCH$_3$ |
| 148 | H | CN | H | —C(CO$_2$CH$_3$)= | 7-CH$_3$ |
| 149 | H | CN | CH$_3$ | —C(CO$_2$CH$_3$)= | 7-CH$_3$ |
| 150 | H | CN | C$_6$H$_5$ | —C(CN)= | H |
| 151 | H | CN | H | —C(COC$_6$H$_5$)= | 7-CH$_3$ |
| 152 | H | CN | H | —C(COC$_6$H$_5$)= | 7-NHCOCH$_3$ |
| 153 | CH$_2$CO$_2$C$_2$H$_5$ | SO$_2$C$_6$H$_5$ | CH$_3$ | —C(CO$_2$CH$_3$)= | 7-NHCOCH$_3$ |
| 154 | CH$_2$CO$_2$C$_2$H$_5$ | SO$_2$C$_6$H$_5$ | CH$_3$ | —C(CO$_2$CH$_3$)= | 7-CH$_3$ |
| 155 | C$_6$H$_5$ | CN | CH$_3$ | —C(CN)= | 7-CH$_3$ |
| 156 | C$_6$H$_5$ | CN | CH$_3$ | —C(CN)= | 7-CH$_3$ |
| 157 | C$_2$H$_5$ | CN | H | —C(CN)= | 7-CH$_3$ |
| 158 | H | CN | CH$_3$ | —C(CN)= | 7-CH$_3$ |
| 159 | H | CN | CH$_3$ | —C(CN)= | 7-CH$_3$ |
| 160 | H | CN | CH$_3$ | —C(CN)= | 7-CH$_3$ |
| 161 | H | CN | H | —C(CN)= | H |
| 162 | H | CN | 2-thienyl | —C(CN)= | H |
| 163 | H | CN | 2-thienyl | —N= | 7-NHCOCH$_3$ |
| 164 | H | CN | 2-furyl | —N= | 7-CH$_3$ |
| 165 | H | CN | 5-chloro-2-thienyl | —N= | 7-CH$_3$ |
| 166 | H | CN | C$_6$H$_5$ | —N= | 7-CH$_3$ |
| 167 | H | CN | C$_6$H$_5$ | —N= | 7-CH$_3$ |
| 168 | H | CN | C$_6$H$_5$ | —N= | 7-CH$_3$ |
| 169 | H | CN | C$_6$H$_5$ | —N= | 7-CH$_3$ |
| 170 | H | CN | C$_6$H$_5$ | —N= | 7-NHCOC$_6$H$_5$ |
| 171 | H | CN | C$_6$H$_5$ | —C(CN)= | 7-NHCO$_2$C$_2$H$_5$ |
| 172 | H | CN | H | —C(CN)= | 7-NHCOC$_6$H$_5$ |
| 173 | H | CN | H | —C(CN)= | 7-NHCOC$_6$H$_{11}$ |
| 174 | H | CN | H | —C(CO$_2$CH$_3$)= | 7-NHSO$_2$CH$_3$ |
| 175 | H | SO$_2$CH$_3$ | H | —C(CN)= | 7-NHCONHC$_2$H$_5$ |
| 176 | H | CN | H | —C(CN)= | 7-Cl |

COLORANTS OF FORMULA III

TABLE 3-continued

| Ex. No. | $R_5$ | $R_7$ | $R_8$ | A |
|---|---|---|---|---|
| 124 | $C_2H_5$ | $CH_3$ | $CH_3$ | $-CH(CH_3)-$ |
| 125 | $C_2H_5$ | $CH_3$ | $CH_3$ | $-CH(CH_3)-$ |
| 126 | $C_2H_5$ | $CH_3$ | $CH_3$ | $-CH(CH_3)-$ |
| 127 | $C_4H_9$-n | $CH_3$ | H | $-CH_2-$ |
| 128 | $C_2H_5$ | $CH_3$ | $CH_3$ | $-CH(CH_3)-$ |
| 129 | $CH_2CH_2OH$ | $CH_3$ | H | $-CH(CH_3)-$ |
| 130 | $C_4H_9$-n | H | H | $-CH_2-$ |
| 131 | $C_2H_5$ | $CH_3$ | H | $-CH_2-$ |
| 132 | $CH_2CH_2CH_2CONH_2$ | $CH_3$ | $CH_3$ | $-CH(CH_3)_2-$ |
| 133 | $CH_2CH_2OC_6H_5$ | H | H | $-CH_2-$ |
| 134 | $CH_2CH_2SO_2CH=CH_2$ | $CH_3$ | H | $-CH_2-$ |
| 135 | $CH_2CH=CH_2$ | $CH_3$ | H | $-CH_2-$ |
| 136 | $CH_2CH_2CH_2SO_2CH_3$ | $CH_3$ | H | $-CH_2-$ |
| 137 | $C_2H_5$ | H | H | $-O-$ |
| 138 | $C_2H_4OCOCH_3$ | $CH_3$ | H | $-O-$ |
| 139 | $CH_2CH_2OC_2H_5$ | $CH_3$ | H | $-O-$ |
| 140 | $C_2H_5$ | H | H | $-O-$ |
| 141 | $C_4H_9$-n | $CH_3$ | H | $-O-$ |
| 142 | $C_2H_5$ | $CH_3$ | $CH_3$ | $-CH(CH_3)-$ |
| 143 | $CH_2CH_2OH$ | $CH_3$ | $CH_3$ | $-CH(CH_3)-$ |
| 144 | $C_2H_5$ | H | H | $-O-$ |
| 145 | $C_2H_5$ | H | H | * |
| 146 | $C_2H_5$ | $CH_3$ | H | * |
| 147 | $C_2H_5$ | $CH_3$ | H | * |
| 148 | $C_2H_4OCOCH_3$ | $CH_3$ | H | * |
| 149 | $C_4H_9$-n | $CH_3$ | H | * |
| 150 | $CH_2C_6H_{11}$ | H | H | * |
| 151 | $CH_2CH_2C_6H_5$ | H | H | * |
| 152 | $CH_2CH(CH_3)_2$ | $CH_3$ | $CH_3$ | $-CH(CH_3)-$ |
| 153 | H | $CH_3$ | $CH_3$ | $-CH(CH_3)-$ |
| 154 | $C_2H_5$ | $CH_3$ | $CH_3$ | $-CH(CH_3)-$ |
| 155 | $CH_2CH_2NHCOCH=CH_2$ | H | H | $-CH(CH_3)-$ |
| 156 | $CH_2CH(OH)CH_2OH$ | $CH_3$ | H | $-CH_2-$ |
| 157 | $CH_2CN(OH)CH_2OH$ | $CH_3$ | H | $-O-$ |
| 158 | $CH_2CH_2OCH_2CH_2OC_2H_5$ | $CH_3$ | H | $-OH(CH_3)-$ |
| 159 | $CH_2CH_2OCH_2CH_2CN$ | $CH_3$ | H | $-O-$ |
| 160 | $CH_2CH_2OCH_2CH_2OH$ | $CH_3$ | H | $-CH_2-$ |
| 161 | $CH_2CH_2OCH_2CH_2OCOCH_3$ | H | H | $-CH_2-$ |
| 162 | $CH_2CH_2CN$ | $CH_3$ | H | $-CH_2-$ |
| 163 | $C_2H_5$ | $CH_3$ | $CH_3$ | $-CH(CH_3)-$ |
| 164 | $CH_2CH_2SO_2CH_2CH_2N\begin{matrix}COCH_2\\COCH_2\end{matrix}$ | H | H | $-CH_2-$ |
| 165 | $CH_2CH_2SO_2CH_2CH_2-S-C_6H_5$ | $CH_3$ | H | $-CH_2-$ |
| 166 | $CH_2CH_2S-C\begin{matrix}N-NH\\\phantom{x}\\N\end{matrix}CH$ | $CH_3$ | H | $-O-$ |
| 167 | $CH_2CH_2SO_2NH_2$ | $CH_3$ | H | $-O-$ |
| 168 | $CH_2CH_2SO_2N(C_2H_4OH)_2$ | $CH_3$ | H | $-CH_2-$ |
| 169 | $CH_2CH_2CH_2NHSO_2CH_3$ | $CH_3$ | H | $-CH_2-$ |
| 170 | $C_2H_5$ | $CH_3$ | $CH_3$ | $-CH(CH_3)-$ |
| 171 | $C_8H_{17}$-n | H | H | $-CH_2-$ |
| 172 | $C_4H_9$-n | $CH_3$ | H | $-CH_2-$ |
| 173 | $CH_2CH_2N\begin{matrix}COCH_2\\COCH_2\end{matrix}$ | $CH_3$ | H | $-CH_2-$ |

TABLE 3-continued

| 174 | CH₂CH₂N(COCH₂)(COS)* | CH₃ | H | —CH₂— |
| 175 | CH₂CH₂OC₂H₅ | CH₃ | CH₃ | —CH(CH₃)— |
| 176 | C₂H₅ | CH₃ | H | —CH₂— |

*The asterisk is used to represent a covalent bond to form an indoline ring.

We claim:

1. A compound of Formula (III)

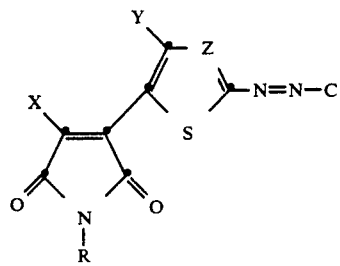

wherein

R is hydrogen; $C_1-C_8$ alkyl; $C_1-C_8$ alkyl substituted with at least one group selected from the list consisting of halo, hydroxy, $C_1-C_6$ alkoxy, $C_1-C_6$ alkanoyloxy, $C_5-C_7$ cycloalkyl, cyano, $C_1-C_6$ carbalkoxy, phenyl, phenyl substituted by one or two groups selected from the list consisting of $C_1-C_6$ alkyl, $C_1-C_6$ alkoxy, $C_1-C_6$ alkoxycarbonyl, $C_1-C_6$ alkanoyloxy, $C_1-C_6$ alkanoylamino, halo, cyano, $C_1-C_6$ alkylsulfonyl, and hydroxy, phenoxy, phenoxy substituted with one or two group selected from the list consisting of $C_1-C_6$ alkyl, $C_1-C_6$ alkoxy, $C_1-C_6$ alkoxycarbonyl, $C_1-C_6$ alkanoyloxy, $C_1-C_6$ alkanoylamino, halo, cyano, $C_1-C_6$ alkylsulfonyl, and hydroxy, or R is $C_3-C_8$ alkenyl; $C_3-C_8$ alkynyl; $C_5-C_7$ cycloalkyl, $C_5-C_8$ cycloalkyl substituted with one or two groups selected from the list consisting of $C_1-C_4$ alkyl, $C_1-C_4$ alkoxy, hydroxy, and $C_1-C_4$ alkanoyloxy; phenyl; or phenyl substituted by one or two groups selected from the list consisting of $C_1-C_6$ alkyl, $C_1-C_6$ alkoxy, $C_1-C_6$ alkoxycarbonyl, $C_1-C_6$ alkanoyloxy, $C_1-C_6$ alkanoylamino, halo, cyano, $C_1-C_6$ alkylsulfonyl, and hydroxy;

X is cyano, $C_1-C_8$ alkylsulfonyl, phenylsulfonyl, or phenylsulfonyl substituted by one or two groups selected from the list consisting of $C_1-C_6$ alkyl, $C_1-C_6$ alkoxy, $C_1-C_6$ alkoxycarbonyl, $C_1-C_6$ alkanoyloxy, $C_1-C_6$ alkanoylamino, halo, cyano, $C_1-C_6$ alkylsulfonyl, and hydroxy;

Y is hydrogen; $C_1-C_4$ alkyl; $C_5-C_7$ cycloalkyl; halogen; phenyl; phenyl substituted b one or two groups selected from the list consisting of $C_1-C_6$ alkyl, $C_1-C_6$ alkoxy, $C_1-C_6$ alkoxycarbonyl, $C_1-C_6$ alkanoyloxy, $C_1-C_6$ alkanoylamino, halo, cyano, $C_1-C_6$ alkylsulfonyl, and hydroxy; 2-thienyl; 2-thienyl substituted with one or two halogen $C_1-C_4$ alkyl, or $C_1-C_4$ alkoxy, or Y is 2-furanyl;

Z is nitrogen or a group of the formula —C(R₁)=, wherein R₁ is cyano, —CO₂R₂, —COR₃, —CONHR₂, or —SO₂R₃, wherein R₂ is hydrogen; $C_1-C_8$ alkyl; $C_1-C_8$ alkyl substituted with at least one group selected from the list consisting of halo, hydroxy, $C_1-C_6$ alkoxy, $C_1-C_6$ alkanoyloxy, $C_5-C_7$ cycloalkyl, cyano, $C_1-C_6$ carbalkoxy, phenyl, phenyl substituted by one or two groups selected from the list consisting of $C_1-C_6$ alkyl, $C_1-C_6$ alkoxy, $C_1-C_6$ alkoxycarbonyl, $C_1-C_6$ alkanoyloxy, $C_1-C_6$ alkanoylamino, halo, cyano, $C_1-C_6$ alkylsulfonyl, and hydroxy; phenoxy; and phenoxy substituted with one or two groups selected from the list consisting of $C_1-C_6$ alkyl, $C_1-C_6$ alkoxy, $C_1-C_6$ alkoxycarbonyl, $C_1-C_6$ alkanoyloxy, $C_1-C_6$ alkanoylamino, halo, cyano, $C_1-C_6$ alkylsulfonyl, and hydroxy; or R₂ is $C_5-C_7$ cycloalkyl; $C_3-C_8$ alkenyl; phenyl; or phenyl substituted by one or two groups selected from the list consisting of $C_1-C_6$ alkyl, $C_1-C_6$ alkoxy, $C_1-C_6$ alkoxycarbonyl, $C_1-C_6$ alkanoyloxy, $C_1-C_6$ alkanoylamino, halo, cyano, $C_1-C_6$ alkylsulfonyl, and hydroxy; and R₃ is $C_1-C_8$ alkyl; phenyl; or phenyl substituted by one or two groups selected from the list consisting of $C_1-C_6$ alkyl, $C_1-C_6$ alkoxy, $C_1-C_6$ alkoxycarbonyl, $C_1-C_6$ alkanoyloxy, $C_1-C_6$ alkanoylamino, halo, cyano, $C_1-C_6$ alkylsulfonyl, and hydroxy;

C is selected from the following formulae;

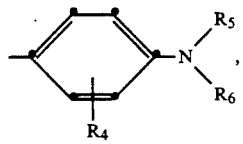

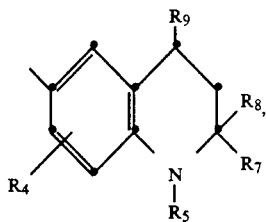

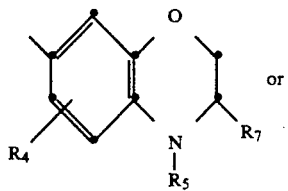

or

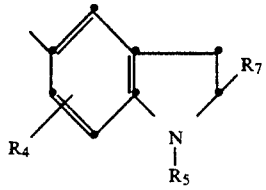

wherein:

$R_4$ is hydrogen or 1-2 groups selected from $C_1-C_4$ alkyl, $C_1-C_4$ alkoxy, halogen, $NHCOR_2$, $NHSO_2R_3$, $NHCO_2R_3$ or $NHCONHR_2$, wherein $R_2$ and $R_3$ are as defined previously;

$R_5$ and $R_6$ are selected from hydrogen; $C_1-C_8$ alkyl; $C_1-C_8$ alkyl substituted with one or more groups selected from the list consisting of $C_5-C_7$ cycloalkyl; $C_5-C_7$ cycloalkyl substituted with one or two of $C_1-C_6$ alkyl, $C_1-C_6$ alkoxy or halogen; phenyl; phenyl substituted with one or two of $C_1-C_6$ alkyl, $C_1-C_6$ alkoxy, $C_1-C_6$ alkoxycarbonyl, halogen, $C_1-C_6$ alkanoylamino, cyano, nitro, or $C_1-C_6$ alkylsulfonyl; cyano; hydroxy; halogen; 2-pyrrolidino; phthalimidino; vinylsulfonyl; acrylamido; o-benzoic sulfimido; $C_1-C_6$ alkoxy; $C_1-C_6$ alkoxy-$C_1-C_6$ alkoxy; cyano $C_1-C_6$ alkoxy; hydroxy $C_1-C_6$ alkoxy; phenoxy; phenoxy substituted with $C_1-C_6$ alkyl, $C_1-C_6$ alkoxy, or halogen; groups of the formulae:

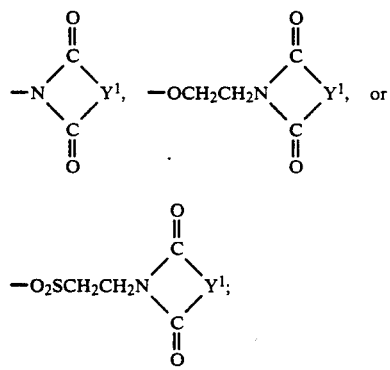

wherein $Y^1$ is selected from o-phenylene; o-phenylene substituted with $C_1-C_6$ alkyl, $C_1-C_6$ alkoxy, halogen or nitro; $C_2-C_3$ alkylene; —O—CH$_2$—; —OCH$_2$CH$_2$—; —CH$_2$OCH$_2$—; —S—CH$_2$—; —CH$_2$SCH$_2$—; —NHCH$_2$—; —NHCH$_2$CH$_2$—; —N(alkyl)CH$_2$—; —N(alkyl)CH$_2$CH$_2$— or —NHC(C$_6$H$_5$)$_2$—; groups of the formulae:

—S—R$_{10}$, —SO$_2$C$_2$H$_4$SR$_{10}$, 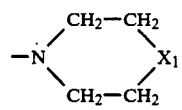 or

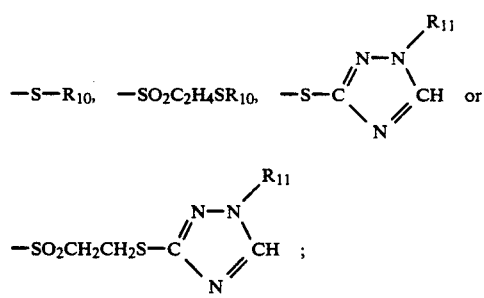

wherein $R_{10}$ is selected from $C_1-C_6$ alkyl; $C_5-C_7$ cycloalkyl; phenyl; phenyl substituted with one or more groups selected from $C_1-C_6$ alkyl, $C_1-C_6$ alkoxy or halogen; a heterocyclic ring selected from the group consisting of pyridyl, pyrimidinyl; benzoxazolyl; benzothiazolyl; benzimidazolyl; 1,3,4-thiadiazolyl, 1,3,4-oxadiazolyl; and said heterocyclic rings substituted with one or more groups selected from $C_1-C_6$ alkyl, $C_1-C_6$ alkoxy or halogen; wherein $R_{11}$ is selected from hydrogen, lower alkyl or benzyl; groups of the formulae:

—SO$_2$R$_{12}$; —SO$_2$N(R$_{13}$)R$_{14}$; —CON(R$_{13}$)R$_{14}$; N(R$_{13}$)COR$_{14}$; OCOR$_{13}$; OCO$_2$R$_{13}$; OCON(R$_{13}$)R$_{14}$ wherein $R_{12}$ is selected from $C_5-C_7$ cycloalkyl; $C_5-C_7$ cycloalkyl substituted with $C_1-C_6$ alkyl; allyl; phenyl; phenyl substituted with one or two groups selected from $C_1-C_6$ alkyl, $C_1-C_6$ alkoxy or halogen; $C_1-C_6$ alkyl; $C_1-C_6$ alkyl substituted with one or more groups selected from $C_1-C_6$ alkoxy, halogen, cyano, $C_5-C_7$ cycloalkyl, phenyl, phenoxy, $C_1-C_6$ alkylthio or $C_1-C_6$ alkylsulfonyl; $R_{13}$ and $R_{14}$ are each independently selected from hydrogen or those groups represented by $R_{12}$;

or $R_5$ and $R_6$ are selected from $C_3-C_8$ alkenyl; $C_3-C_8$ alkynyl; $C_5-C_7$ cycloalkyl; $C_5-C_7$ cycloalkyl substituted with one or two groups selected from the list consisting of $C_1-C_4$ alkyl, $C_1-C_4$ alkoxy, hydroxy, and $C_1-C_4$ alkanoyloxy; phenyl; phenyl substituted by one or two groups selected from the list consisting of $C_1-C_6$ alkyl, $C_1-C_6$ alkoxy, $C_1-C_6$ alkoxycarbonyl, $C_1-C_6$ alkanoyloxy, $C_1-C_6$ alkanoylamino, halo, cyano, $C_1-C_6$ alkylsulfonyl, and hydroxy;

or $R_5$ and $R_6$ may be combined with the nitrogen to which they are attached to form a radical having the formula $$-N\begin{array}{c}CH_2-CH_2\\ \\CH_2-CH_2\end{array}X_1$$

wherein $X_1$ is selected from —CH$_2$—, —O—, —S—, —SO$_2$—, —CO—, —CO$_2$—, —NH—, —N—COC$_1$-C$_4$ alkyl or —N—SO$_2$C$_1$-C$_4$ alkyl; and $R_7$, $R_8$ and $R_9$ are hydrogen or $C_1-C_4$ alkyl.

2. The compound of claim 1, wherein R is hydrogen.

3. The compound of claim 1, wherein R is hydrogen; X is cyano; Y is hydrogen, methyl, or phenyl, and Z is —N=.

4. The compound of claim 1, wherein R is hydrogen; X is cyano; Y is hydrogen, methyl, or phenyl; and Z is —C(CO$_2$C$_1$-C$_8$ alkyl)= or —C(CN)=.

5. The compound having the formula

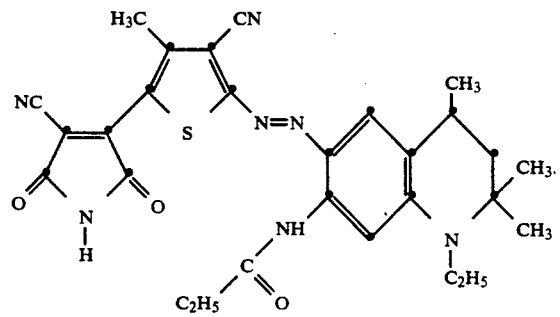

6. The compound having the formula

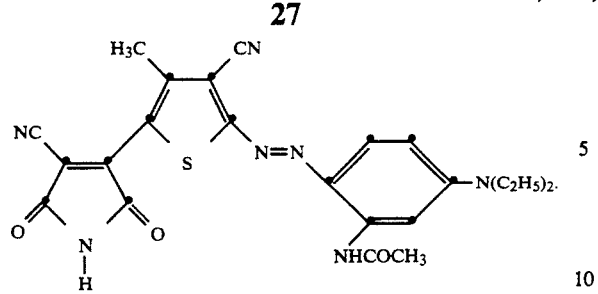
* * * * *